US006649156B1

(12) United States Patent
Chane-Ching

(10) Patent No.: US 6,649,156 B1
(45) Date of Patent: Nov. 18, 2003

(54) ORGANIC SOL AND SOLID COMPOUND BASED ON CERIUM OXIDE AND AN AMPHIPHILIC COMPOUND AND METHOD FOR PREPARING SAME

(75) Inventor: Jean-Yves Chane-Ching, Eaubonne (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/913,709

(22) PCT Filed: Feb. 10, 2000

(86) PCT No.: PCT/FR00/00330
§ 371 (c)(1),
(2), (4) Date: Nov. 26, 2001

(87) PCT Pub. No.: WO00/49098
PCT Pub. Date: Aug. 24, 2000

(30) Foreign Application Priority Data

Feb. 17, 1999 (FR) .............................................. 99 01939

(51) Int. Cl.[7] .......................... A61K 7/42; B01F 17/02; B01F 17/44; C09D 17/00; C10L 1/12
(52) U.S. Cl. ..................... 424/70.9; 44/364; 106/14.44; 516/33; 524/403
(58) Field of Search ........................ 516/33; 524/403; 424/70.9; 106/14.44; 44/364

(56) References Cited

U.S. PATENT DOCUMENTS 5,376,304 A * 12/1994 Yamamoto et al. ........... 516/33
5,688,439 A * 11/1997 Chopin et al. ................ 516/33
5,695,747 A * 12/1997 Forestier et al. ....... 424/70.9 X
5,718,907 A * 2/1998 Labarre ................... 524/403 X
5,733,895 A * 3/1998 Forestier et al. ....... 424/70.9 X
6,136,048 A * 10/2000 Birchem et al. .......... 516/33 X
6,183,728 B1 * 2/2001 Forestier et al. ....... 424/70.9 X
6,210,451 B1 * 4/2001 Chopin et al. ............. 516/33 X
6,271,269 B1 * 8/2001 Chane-Ching et al. ........ 516/33
6,375,936 B1 * 4/2002 Allard et al. .......... 424/70.9 X

FOREIGN PATENT DOCUMENTS

EP          0 671 205 A     9/1995

* cited by examiner

Primary Examiner—Richard D. Lovering
(74) Attorney, Agent, or Firm—Burns, Doane, Swecker & Mathis, L.L.P.

(57) ABSTRACT

An organic sol containing: cerium oxide particles; an organic liquid phase; and at least one amphiphilic compound chosen from polyoxyethylenated alkyl ethers of carboxylic acids, polyoxyethylenated alkyl ether phosphates, dialkyl sulphosuccinates and quaternary ammonium compounds. A process for preparing the sol is characterized in that the abovementioned amphiphilic compound and the organic liquid phase are mixed together and the cerium oxide particles are then dispersed in the mixture obtained. According to a second variant, a mixture of cerium oxide and of at least one abovementioned amphiphilic compound is formed and the said mixture is then dispersed in the organic liquid phase.

14 Claims, No Drawings

ORGANIC SOL AND SOLID COMPOUND BASED ON CERIUM OXIDE AND AN AMPHIPHILIC COMPOUND AND METHOD FOR PREPARING SAME

The present application is filed under 35 U.S.C §371 and is based on International Application PCT/FR00/00330 with an international filing date of Feb. 10, 2000, and which was published as WO 00/49098 on Aug. 24, 2000.

The present invention relates to an organic sol and to a solid compound based on cerium oxide and on an amphiphilic compound, and to processes for their preparation.

Sols or colloidal dispersions of cerium oxide in organic media are known. However, the processes for preparing these sols do not allow a large variety to be obtained. The sols prepared by these processes are essentially sols in a nonpolar organic medium. The processes of the prior arc generally proceed via the preparation of an aqueous sol in a first stage, and, in a second stage, placing this aqueous sol in contact with an organic phase in order to carry out the transfer of the cerium oxide into the organic phase. Such an approach is not suitable for preparing sols in water-miscible polar phases. Now, cerium oxide sols can be used in a multitude of applications, such as catalysis, anticorrosion coatings and paints. This variety of applications thus gives rise to a need for sols with varied characteristics and of different types from those already known, and also a need for processes suitable for their preparation.

One object of the invention is to provide such organic sols.

Another subject of the invention is a process for gaining access to a large range of organic sols and in particular to sols in polar solvents.

With this aim, the organic sol of the invention is characterized in that it comprises cerium oxide particles; an organic liquid phase and at least one amphiphilic compound chosen from polyoxyethylenated alkyl ethers of carboxylic acids, polyoxyethylenated alkyl ether phosphates, dialkyl sulphosuccinates and quaternary ammonium compounds.

The invention also relates to a process for preparing such a sol, which, according to a first variant, is characterized in that the abovementioned amphiphilic compound and the organic liquid phase are mixed together and the cerium oxide particles are then dispersed in the mixture obtained. According to a second variant, the process is characterized in that a mixture of cerium oxide and of at least one abovementioned amphiphilic compound is formed and the said mixture is them dispersed in the organic liquid phase.

The sols of the invention have the advantage of being able to exist in a wide range of solvents: polar or non-polar solvents.

Other characteristics, details and advantages of the invention will emerge even more fully on reading the description which follows, as well as the various concrete, but in no way limiting, examples intended to illustrate it.

For the remainder of the description, the expression "sol or colloidal dispersion of cerium oxide" denotes any system consisting of fine solid particles of colloidal size based on cerium oxide and/or hydrated cerium oxide (hydroxide) suspended in a liquid phase, it moreover being possible for the said species optionally to contain residual amounts of bound or adsorbed ions such as, for example, nitrates, acetates, citrates or ammoniums. It will be noted that, in such dispersions, the cerium can be either totally in the form of colloids, or simultaneously in the form of ions and in the form or colloids.

The cerium oxide particles generally have a mean diameter of not more than 100 nm, more particularly of not more than 50 nm and even more particularly of not more than 20 nm. For example, this diameter can be between 5 and 10 nm. It is specified here that the expression "mean diameter of the particles or colloids" should be understood as denoting the mean hydrodynamic diameter of these particles or colloids, and as determined by quasi-elastic light scattering according to the method described by Michael L. McConnell in the review Analytical Chemistry 53, No. 8, 1007 A, (1981).

Finally, the cerium is generally present in the form of cerium IV. The cerium can also be present in the form of a mixture of cerium III and cerium IV in any respective proportions.

The organic liquid phase in the sol of the invention can be based on an organic liquid or a mixture of organic liquids of very varied nature.

The organic liquid or solvent can be an inert aliphatic or cycloaliphatic hydrocarbon, or a mixture thereof, such as, for example, mineral or petroleum spirits which can also contain aromatic components. Mention may be made, as a guide, of hexane, heptane, octane, nonane, decane, cyclohexane, cyclopentane, cycloheptane and liquid naphthenes. Aromatic solvents such as benzene, toluene, ethylbenzene and xylenes are also suitable, as are petroleum fractions of the Isopar or Solvesso type (registered trade marks of the company Exxon), in particular Solvesso 100 which essentially contains a mixture of methylethylbenzene and trimethylbenzene, and Solvesso 150 which comprises a mixture of alkylbenzenes, in particular of dimethylethylbenzene and tetramethylbenzene.

It is also possible to use chlorinated hydrocarbons such as chlorobenzene, dichlorobenzene or chlorotoluene, as well as aliphatic and cycloaliphatic ethers such as diisopropylether and dibutylether, and aliphatic and cycloaliphatic ketones such as methyl isobutyl ketone, diisobutyl ketone and mesityl oxide.

It is also possible to use ketones, such as acetone, aldehydes, nitrogenous solvents such as acetonitrile, alcohols, acids and phenols.

Esters can also be envisaged. As esters which can be used, mention may be made in particular of those derived from the reaction of acids with C1 to C8 alcohols and in particular palmitates of secondary alcohols such as isopropanol. The acids from which these esters are derived can be aliphatic carboxylic acids, aliphatic sulphonic acids, aliphatic phosphonic acids, alkylarylsulphonic acids and alkylarylphosphonic acids containing from about 10 to about 40 carbon atoms, and being either natural or synthetic. Examples which may be mentioned are fatty acids of tall oil, of coconut oil, of soybean oil, of tallow oil or of flax oil, oleic acid, linoleic acid, stearic acid and its isomers, pelargonic acid, capric acid, lauric acid, myristic acid, dodecylbenzenesulphonic acid, 2-ethylhexanoic acid, naphthenic acid, hexoic acid, toluenesulphonic acid, toluenephosphonic acid, laurylsulphonlc acid, laurylphosphonic acid, palmitalsulphonic acid and palmitalphosphonic acid.

According to one particularly advantageous characteristic of the sol of the invention, the organic liquid phase is based on a polar solvent or on a mixture of polar solvents. The expression "polar solvent" means solvents which have a dielectric constant $\in$ of greater than 5, as defined in particular in the book "Solvents and Solvent Effects in Organic Chemistry", C. Reichardt, VCH, 1988. This polar solvent can be chosen from halogenated solvents such as dichloromethane; esters such as ethyl acetate, isopropyl palmitate or methoxypropyl acetate; alcohols such as ethanol, butanol or isopropanol; polyols such as propanediol, butanediol or diethylene glycol; ketones such as cyclohexanone or 1-methyl-2-pyrrolidinone.

According to an important characteristic of the invention, the sol also comprises an amphiphilic compound. Without wishing to be bound by an explanation, it may be considered that this amphiphilic compound is adsorbed onto or is in electrostatic interaction with cerium oxide particles or else is complexed therewith.

This compound can be chosen firstly from polyoxyethylenated alkyl ethers of carboxylic acids.

This refers to the products of formula: $R_1—(OC_2H_4)_n—O—R_2$ in which $R_1$ is a linear or branched alkyl radical which comprises in particular 4 to 20 carbon atoms, n is an integer which can range, for example, up to 12, and $R_2$ is a carboxylic acid residue such as, for example, $—CH_2COOH$. Needless to say, it is possible to use these products as a mixture. Examples of amphiphilic compounds of this type which may be mentioned are those sold under the brand name AKYPO® by Kao Chemicals.

The amphiphilic compound can also be chosen from polyoxyethylenated alkyl ether phosphates. This refers to the polyoxyethylenated alkyl phosphates of formula:

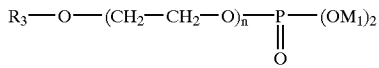

or the polyoxyetnylenated dialkyl phosphates of formula:

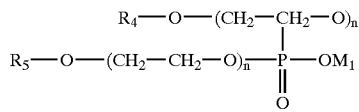

in which $R_3$, $R_4$ and $R_5$, which may be identical or different, represent a linear or branched alkyl radical, in particular of 2 to 20 carbon atoms; a phenyl radical; an alkylaryl radical, more particularly an alkylphenyl radical, with, in partcular, an alkyl chain of 8 to 12 carbon atoms; an arylalkyl radical, more particularly a phenylaryl radical; it being possible for n, the number of ethylene oxides, to range from 2 to 12, for example; $M_1$ represents a hydrogen, sodium or potassium atom. The radical $R_3$ can in particular be a hexyl, octyl, decyl, dodecyl, oleyl or nonylphenyl radical.

Examples of amphiphilic compounds of this type which may be mentioned are those sold under the brand names Lubrophos® and Rhodafac® sold by Rhodia, and in particular the products below:
- the polyoxyethylene (C8–C10)alkyl ether phosphates Rhodafac® RA 600
- the polyoxyethylene tridecyl ether phosphate Rhodafac® RS 710 or RS 410
- the polyoxyethylene oleocetyl ether phosphate Rhodafac® PA 35
- the polyoxyethylene nonylphenyl ether phosphate Rhodafac® PA 17
- the polyoxyethylene (branched)nonyl ether phosphate Rhodafac® RE 610

The amphiphilic compound in the sol of the invention can also be chosen from dialkyl sulphosuccinates, and in particular alkaline dialkyl sulphosuccinates such as sodium dialkyl sulphosuccinates, i.e. the compounds of formula $R_6—O—C(O)—CH_2—CH(SO_3M_2)—C(O)—O—R_7$ in which R6 and R7, which may be identical or different, represent a $C_4$ to $C_{14}$ alkyl radical, for example, and $M_2$ is an alkali metal or a hydrogen.

Examples of compounds of this type which may be mentioned are those sold under the brand name Aerosol® by the company Cyanamid.

As other amphiphilic compounds which are suitable for the present invention, mention may also be made of quaternary ammonium compounds. Mention may be made more particularly of mono-, di- or trialkylammonium compounds, it being possible for one of the radicals attached to the nitrogen atom to be an alkyl radical comprising from 1 to 3 carbon atoms, including these alkyl radicals of 1 to 3 carbon atoms bearing inert substituents, for example halogen, acetate, methyl sulphate, etc., one of the other radicals possibly being a $C_4$ to $C_{20}$ alkyl radical.

The choice of the amphiphilic compound is made as a function of the nature of the organic liquid phase. More specifically, this choice is made by adapting the hydrophilic/lipophilic balance of the amphiphilic compound to the hydrophilic/lipophilic nature of the organic phase. In other words, the more polar the solvent forming part of the organic phase, the more hydrophilic the amphiphilic compound.

The proportion of amphiphilic compound relative to the cerium oxide is adjusted so as to obtain a stable dispersion; it is generally between 2 and 10 molecules per $nm^2$ of area of cerium oxide, assuming an area per complexing head of the cerium cation of between 10 and 80 $\text{Å}^2$.

The sols according to the invention have a cerium compound concentration which can be at least 10% expressed by weight of $CeO_2$ relative to the total weight of the dispersion.

The organic sols thus developed have excellent stability. No decantation is observed after several months.

The water content of the sols of the invention may be not more than 1%, advantageously 1000 ppm, preferably 100 ppm.

The present invention also relates to a solid compound which is characterized in that it comprises a mixture of cerium oxide particles and of at least one amphiphilic compound chosen from those which have been described above.

This solid compound is either in the form of a paste or in the form of a powder. The cerium oxide in this solid compound is in the form of non-aggregated elementary crystallites with a mean size of about 5 nm, or aggregated into aggregates with a mean size which can range from 200 nm to 10 nm approximately, it being possible for these aggregates to form agglomerates which can be deagglomerate. The solid compound has the property of being redispersible, i.e. of being able to give a sol according to the invention and as described above when it is suspended in an organic liquid phase.

That which has been described above, moreover, regarding the nature of the particles of the sol also applies here for the solid compound.

The processes for preparing the solid compound and the sol of the invention will now be described.

The starting material used is any cerium oxide which is capable of giving a sol when it is dispersed in a liquid phase, and in particular any cerium oxide which can;be in the form which has been described above on the subject of the solid compound. By way of example, mention may be made of cerium oxide prepared by thermal hydrolysis.

Thermal hydrolysis is essentially a process in which an aqueous solution is prepared containing a soluble cerium compound; this aqueous solution is reacted with a base; he medium obtained is then heated; the reaction product is recovered and finally, the product recovered is optionally dried. Such a process is described in patent application EP-A-208 580, the teaching of which is incorporated herein.

Water-cerium compounds which may be mentioned more particularly are cerium(IV) salts such as nitrates or ceric ammonium nitrates, for example, which are particularly suitable here, or alternatively organic cerium(IV) salts. Ceric nitrate is preferably used.

The base added to the solution can be an aqueous ammonia solution or a solution of alkali metal (sodium, potassium) hydroxides. The reaction with the base gives a dispersion containing ions and colloids of a cerium compound.

The proportion between this base or basic solution and the cerium salt solution should be such that the degree of neutralization is greater than or equal to 0.01 and less than or equal to 3.0. The expression "degree of neutralizations" (r) means the following ratio:

$$r = \frac{n3 - n2}{n1}$$

in which n1 represents the total number of moles of Ce IV present in the solution after neutralization; n2 represents the number of moles of OH ions effectively needed to neutralize the initial free acidity provided by the aqueous cerium IV salt a solution; and n3 represents the total number of moles of OH ions provided by the addition of the base.

The precipitation of cerium dioxide is carried out by a heat treatment of the dispersion obtained after the reaction with the base. The temperature at which this heat treatment is carried out can be between 80° C. and the critical temperature of the reaction medium in particular between 80° C. and 350° C., preferably between 90° C. and 160° C.

Depending on the temperature conditions selected, this treatment car be carried out either under normal atmospheric pressure or under a pressure such as, for example, the saturating vapour pressure corresponding substantially to the temperature of the heat treatment.

When the treatment temperature selected is above the reflux temperature (under ordinary pressure) of the reaction mixture (i.e. generally above 100° C.), for example selected between 120° C., usually 150° C., and 350°C., the operation is then carried out in a closed chamber which is more particularly a closed reactor more commonly referred to as an autoclave. The aqueous mixture containing the abovementioned species is placed in this chamber, the pressure required resulting merely from heating the reaction medium (autogenous pressure). Under the temperature conditions given above, and in aqueous medium, it can thus be pointed out, for illustrative purposes, that the pressure in the closed reactor ranges between a value of greater than 1 bar ($10^5$ Pa) and 200 bar ($20 \cdot 10^7$ Pa), preferably between 5 bar ($5 \cdot 10^5$ Pa) and 150 bar ($1.5 \cdot 10^7$ Pa). Needless to say, it is also possible to exert an external pressure which then adds to the pressure resulting from the heating.

The heating can be carried out either under an atmosphere of air or under an atmosphere of an inert gas, preferably nitrogen.

The duration of the treatment is not critical, and an thus vary within a wide range, for example between 1 and 48 hours, preferably between 2 and 24 hours.

Similarly, the temperature increase is carried out at a rate which is not critical, and the set reaction temperature can be reached by heating the medium, for example, for between 30 minutes and 4 hours, these values being given entirely as a guide.

After the thermal hydrolysis, a solid precipitate is collected which can be separated from its medium by any conventional solid-liquid separation technique such as, for example, elutriation, filtration, decantation, spin-drying or centrifugation.

It will be noted that it is obviously possible to repeat a heating step (thermal hydrolysis) as defined above, one or more times, in an identical manner or otherwise, in this case using thermal treatment cycles, for example.

The precipitate is then optionally dried.

This precipitate constitutes a starting material which is subsequently used in the processes for preparing the sol of the invention which will be described later.

Mention may be made of another preparation process which can be used to obtain a cerium oxide which can be used as a starting material. This Process comprises the following steps:

a solution or suspension comprising at least one trivalent cerium acetate or chloride is prepared;

the solution is placed in contact with a basic medium and the reaction mixture thus formed is maintained at a basic pH;

the precipitate formed is recovered.

The expression "basic medium" means any medium with a pH of greater than 7. The basic medium will usually be an aqueous solution containing a base. Bases which can be used in particular are products of the hydroxide type. Mention may be made of alkali metal hydroxides or alkaline-earth metal hydroxides. Secondary, tertiary or quaternary amines can also be used. However, amines and aqueous ammonia may be preferred since they reduce the risks of pollution by the alkali metal or alkaline-earth metal cations. Urea may also be mentioned.

The abovementioned mixture and the basic medium can be placed in contact under conditions such that the pH of the reaction mixture thus formed remains basic.

Preferably, this pH value will be at least 9. It may more particularly be not more than 11. Even more particularly, this value may be between 9.5 and 11.

The abovementioned mixture and the basic medium can be placed in contact by introducing the mixture into the basic medium. It is also possible to carry out the placing in contact continuously, the pH condition being achieved by adjusting the respective flow rates of the mixture and of the basic medium.

According to one specific variant of the invention, it is possible to work under conditions such that, during the placing in contact of the mixture with the basic medium, the pH of the reaction medium thus formed is kept constant. Such conditions can be obtained by adding an additional amount of base to the mixture formed during the introduction of the mixture to the basic medium.

The placing in contact is usually carried out at room temperature.

After the reaction, a precipitate or suspension is obtained which can be separated, if necessary, from the reaction mixture by any known means. The separated product can be washed.

The precipitate is then optionally dried.

This precipitate also constitutes a starting material which is used subsequently in the processes which will be described below.

The process for preparing the sol of the invention can be carried out according to a first variant. In this variant, the abovementioned amphiphilic compound and the organic liquid phase are mixed together and the cerium oxide particles are then dispersed in the mixture obtained. It should be noted that it is possible either to introduce the solid particles into the amphiphilic compound/organic phase mixture, or to pour this mixture onto the cerium oxide particles. Once the particles, the amphiphilic compound and the organic phase have been placed together, stirring is carried out until a stable colloidal dispersion is obtained.

A second variant of the process exists. In this case, a mixture of cerium oxide and of at least one abovementioned amphiphilic compound is formed. This mixture can be prepared using any known mechanical means such as blending, in order to obtain a homogeneous paste. A solid compound as defined above is thus obtained. In a second stage, the said mixture is dispersed in the organic liquid phase.

A third variant will now be described, which is more particularly suitable for preparing a sol with a polar organic phase.

This variant, for preparing a sol according to the invention in a organic liquid phase (a) comprises a first step in which a dispersion is formed comprising cerium oxide particles and at least one amphiphilic compound of the abovementioned type in an organic liquid phase (b) based on a solvent of lower polarity than that of the solvent in the organic liquid phase (a). Demixing can be observed during the formation of this dispersion, due to the water which may be present in the starting hydrated cerium oxide. In this case, the demixed water is separated from the rest of the dispersion.

In a second step, the solid phase of the dispersion is separated from the liquid phase (b) thereof. This separation can be carried out by any suitable technique. It is thus possible to carry out the separation by flocculation with an intermediary solvent or alternatively by distillation. After this separation, the solid phase is collected which can be dried and which, depending on the level of drying reached and the nature of the amphiphilic compound, is either in powder form or in paste form and which constitutes a solid compound according to the invention in a final step, the phase or the solid compound thus obtained is redispersed in the organic phase (a) in order thus to obtain the desired sol.

Finally, it will be noted that the sols obtained can undergo a dehydration post-treatment by passing them over a solid desiccant, for example.

The sols of the invention can be used in many applications. Mention may be made of lubrication and ceramics. They can also be used as drying agents in the paints and varnish industry in order to accelerate the drying of unsaturated oils, on a substrate as an anticorrosion agent, or in the preparation of cosmetic compositions, in particular in the preparation of anti-UV creams.

Another advantageous use is that as a combustion additive in liquid fuel and combustibles for power generators, such as internal combustion engines, oil burners or reaction thrusters.

The sols of the invention are more particularly suitable as additives in diesel fuel for diesel engines.

Non-limiting examples will now be given.

EXAMPLE 1

This example illustrates the preparation of a colloidal dispersion of $CeO_2$ in xylene medium.

22.4 g of an amphiphilic compound such as the polyoxyethylenated phosphate ester Rhodafac RS 410 sold by Rhodia, and 100 g of Isopar solvent are placed in a beaker at room temperature.

40 g of hydrated cerium oxide, containing 65.7% $CeO_2$ prepared from a ceric nitrate solution at 100° C., by the thermal hydrolysis process described above and as in example 1 of EP-A-208 580, are gradually added. The mixture is made up to 200 g in total (mass of the hydrate+amphiphilic compound+Isopar) with Isopar.

The mixture is left stirring until a stable colloidal dispersion is obtained.

The small amount of aqueous phase obtained is separated out by demixing and the dispersion thus obtained is flocculated by addition of acetone. The precipitate obtained is collected by centrifugation and is left to dry at room temperature.

4 g of the product obtained are redispersed in 16 g of xylene at room temperature. A colloidal dispersion is thus obtained which is stable towards separation of the phases by settling.

EXAMPLE 2

This example illustrates the preparation of a colloidal dispersion of $CeO_2$ in $CH_2Cl_2$ medium.

30.5 g of an amphiphilic compound such as the polyoxyethylenated carboxylic acid alkyl ether AKYPO LF4, sold by Kao Chemicals GmbH, and 100 g of $CH_2Cl_2$ are placed in a beaker at room temperature. 40 g of hydrated cerium oxide containing 65.7% $CeO_2$ like the product described in Example 1, are gradually added and the mixture is made up to 200 g in total with $CH_2Cl_2$. This mixture is stirred at room temperature until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic compound.

4 g of this product thus obtained are dispersed in 16 g of $CH_2Cl_2$. A colloidal dispersion is obtained. By quasi-elastic light scattering, a hydrodynamic diameter of the colloids of between 5 and 10 nm is determined.

EXAMPLE 3

This example illustrates the preparation of a colloidal dispersion of $CeO_2$ in ethyl acetate medium.

38.6 g of an amphiphilic compound Rhodafac RS 710, sold by Rhodia, and 200 g of $CH_2Cl_2$ are placed in a beaker at room temperature. 40 g of hydrated cerium oxide containing 65.7% $CeO_2$, like the product described in Example 1, are then gradually added and the mixture is made up to 300 g in total with $CH_2Cl_2$. This mixture is left stirring until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic agent.

4 a of this product thus obtained are dispersed in 16 g of ethyl acetate. A colloidal dispersion is obtained. By quasi-elastic light scattering, a hydrodynamic diameter of the colloids of between 5 and 10 nm is determined.

EXAMPLE 4

This example illustrates the preparation of a colloidal dispersion of $CeO_2$ in ethyl acetate medium.

30.5 g of an amphiphilic compound AKYPO LF4 are placed in a beaker and 100 g of $CH_2Cl_2$ are added. 40 g of the cerium oxide of Example 1 are gradually added and this mixture is made up to 200 g in total with $CH_2Cl_2$. The mixture is stirred at room temperature until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic agent.

4 g of this product thus obtained are dispersed in 16 g of ethyl acetate. A colloidal dispersion is obtained. By quasi-elastic light scattering, a hydrodynamic diameter of the colloids of between 5 and 10 nm is determined.

EXAMPLE 5

This example illustrates the preparation of a colloidal dispersion of $CeO_2$ in methoxypropyl acetate medium.

38.6 g of an amphiphilic compound Rhodafac RS 710 and 200 g of $CH_2Cl_2$ are placed in a beaker at room temperature. 40 g of the cerium oxide of Example 1 are then gradually added and this mixture is made up to 300 g in total with $CH_2Cl_2$. The mixture is left stirring until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic agent.

4 g of this product thus obtained are dispersed in 16 g of methoxypropyl acetate. A colloidal dispersion is obtained. By quasi-elastic light scattering, a hydrodynamic diameter of the colloids of between 10 and 20 nm is determined.

The percentage of water in the dispersion is 0.9%.

EXAMPLE 6

This example illustrates the preparation of a colloidal dispersion of $CeO_2$ in ethanol medium.

36.6 g of an amphiphilic compound Rhodafac RS 710, sold by Rhodia, and 200 g of $CH_2Cl_2$ are placed in a beaker at room temperature. 40 g of the cerium oxide of the example are then added and this mixture is made up to 300 g in total with $CH_2Cl_2$. The mixture is left stirring until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic agent.

4 g of this product thus obtained are dispersed in 16 g of absolute ethanol. A colloidal dispersion is obtained. By quasi-elastic light scattering, a hydrodynamic diameter of the colloids of between 5 and 10 nm is determined.

EXAMPLE 7

This example illustrates the preparation of a colloidal dispersion of $CeO_2$ in ethanol medium.

30.5 g of an amphiphilic compound AKYPO LF4 and 100 g of $CH_2Cl_2$ are placed in a beaker at room temperature. 40 g of the cerium oxide of Example 1 are then gradually added and this mixture is made up to 200 g in total with $CH_2Cl_2$. The mixture is stirred at room temperature until a stable colloidal dispersion is obtained.

Demixing of a small volume of a clear colourless phase (released water) is observed, and is separated out.

The dispersion thus obtained is evaporated at room temperature. A paste is obtained containing ceric oxide nanoparticles and the amphiphilic agent.

4 g of this product thus obtained are dispersed in 16 g of absolute ethanol. A colloidal dispersion is obtained. By quasi-elastic light scattering, a hydrodynamic diameter of the colloids of between 5 and 10 nm is determined.

What is claimed is:

1. Organic sol, comprising:
    cerium oxide particles;
    an organic liquid phase;
    at least one amphiphilic compound selected from the group consisting of: polyoxyethylenated alkyl ethers of carboxylic acids; polyoxyethylenated alkyl, phenyl or alkylaryl ether phosphates and dialkyl sulphosuccinates.

2. Sol according to claim 1, wherein the organic liquid phase is based on a polar solvent.

3. Sol according to claim, 1, wherein the amphiphilic compound is selected from the group consisting of sodium dialkyl sulphosuccinates.

4. Sol according to claim 1, wherein the amphiphilic compound is polyoxyethylenated alkyl or alkylaryl ether phosphates.

5. Sol according to claim 1, wherein the organic liquid phase comprises a polar solvent, the polar solvent is selected from the group consisting of halogenated solvents, esters and alcohols.

6. An additive in diesel fuel for diesel engines comprising an effective amount of the sol according to claim 1.

7. A cosmetic composition comprising an effective amount of the sol according to claim 1 and a cosmetically acceptable carrier therefor.

8. Process for preparing a sol according to claim 1, comprising forming a mixture of cerium oxide and of at least one abovementioned amphiphilic compound and dispersing said mixture in the organic liquid phase.

9. Process for preparing a sol according to claim 1, comprising forming a dispersion comprising cerium oxide particles and at least one of the amphiphilic compounds in a first organic liquid phase based on a solvent of lower polarity than that of a second organic liquid phase; separating the solid phase from the first organic liquid phase; and dispersing the solid phase thus obtained in the second organic liquid phase.

10. Process for preparing a sol according to claim 1, comprising mixing the amphiphilic compound and the organic liquid phase together and dispersing the cerium oxide particles in the mixture obtained.

11. Preparation process according to claim 10, comprising using a starting cerium oxide which has been obtained by a process in which a solution or suspension comprising at least one cerium acetate or chloride is prepared; the solution is placed in contact with a basic medium and the reaction mixture thus formed is maintained at a basic pH; and the precipitate formed is recovered.

12. Preparation process according claim 10, comprising using a starting cerium oxide which has been obtained by a process in which an aqueous solution is prepared containing a soluble cerium compound; this aqueous solution is reacted with a base; the medium obtained is then heated; the reaction product is recovered and, finally, the product recovered is optionally dried.

13. Process according to claim 12, wherein the soluble cerium compound is organic or inorganic cerium (IV) salts.

14. Solid compound, comprising a mixture of cerium oxide particles and of at least one amphiphilic compound selected from the group consisting of polyoxyethylenated alkyl ethers of carboxylic acids, polyoxyethylenated alkyl, phenyl or alkylaryl ether phosphates and, dialkyl sulphosuccinates.

* * * * *